United States Patent [19]

Olsson

[11] Patent Number: 5,019,497

[45] Date of Patent: May 28, 1991

[54] HUMAN SQUAMOUS LUNG CARCINOMA CELL SPECIFIC ANTIGENS AND ANTIBODIES

[76] Inventor: Lennart Olsson, Rigshospitalet 9, Blegdamsvej, Copenhagen, Denmark, DK-2100

[21] Appl. No.: 215,056

[22] Filed: Jul. 5, 1988

Related U.S. Application Data

[63] Continuation of Ser. No. 701,322, Feb. 13, 1985, abandoned.

[51] Int. Cl.$^5$ .................. G01N 33/53; G01N 33/577; C07K 15/14; C12N 15/00
[52] U.S. Cl. ........................... 435/7.23; 435/172.2; 435/240.27; 435/975; 435/948; 436/64; 436/501; 436/536; 436/548; 436/808; 436/813; 530/350; 530/387; 530/388; 530/395; 530/808; 530/828; 530/848; 536/1.1
[58] Field of Search ............... 436/548, 544, 545, 518, 436/808, 813, 501, 536, 64; 435/7, 68, 172.2, 240.26, 240.27, 810, 948; 424/85, 86, 87, 88; 530/387, 388, 350, 395, 403, 412, 808, 810, 828, 848; 536/1.1; 514/2

[56] References Cited

PUBLICATIONS

Martensson, S., et al., Cancer Res., 48:2125–2131, (1988).

*Primary Examiner*—Esther L. Kepplinger
*Assistant Examiner*—Florima B. Hoffer
*Attorney, Agent, or Firm*—Bertram I. Rowland

[57] ABSTRACT

Methods and compositions are provided for detecting antigens having a specific epitope associated with squamous lung carcinoma. The antigen may be found at lesion sites or in the blood as indicative of the squamous lung carcinoma.

Specific antibodies may be used for the detection of the antigen and in therapy.

The mouse hybridoma 43-9F producing IgM monoclonal antibody 43-9F and SLC cell RH-SLC-L11 were deposited at The PHLS Centre for Applied Microbiology and Research, Porton Down, Salisbury, U.K. on Jan. 31, 1985 and given Accession Nos. 85013101 and 85061403, respectively.

27 Claims, No Drawings

HUMAN SQUAMOUS LUNG CARCINOMA CELL SPECIFIC ANTIGENS AND ANTIBODIES

This is a continuation of application Ser. No. 701,322, filed Feb. 13, 1985, now abandoned.

BACKGROUND OF THE INVENTION

1. Field of the Invention

Cancer cells synthesize unusual and sometimes highly specific proteins and glycolipids that in many cases have been identified as fetal or embryonic macromolecules apparently produced in the cancer cell after either aberrant activation or failure to deactivate genes normally silent in differentiated cells. Some of these gene-products may influence the abnormal proliferative properties of the cancer cells. Sensitive methods are needed for identifying the unusual cellular compounds with high tumor specificity, because they may provide signals for early cancer detection and perhaps for advancing understanding of the transformation process.

In no area is this more needed than in the case of malignant lung neoplasms. Particularly, squamous cell carcinomas, which represent about 50-60% in males of malignant lung neoplasms have proven very difficult to treat, since at the time of diagnosis, the disease is normally no longer localized. It could therefore be extremely important in the treatment of the disease to have a means for early diagnosis.

2. Description of the Prior Art

Olsson et al., Cancer (1984) 54:1757-1765 report monoclonal antibodies for lung carcinoma. Antisera and monoclonal antibodies with reactivity to human lung cancer cells have been described by Kelly and Levy, Br. J. Cancer (1977) 35:828-833; Cuttita et al., Proc. Natl. Acad. Sci. USA (1981) 78:4591-4595; Braatz et al., Cancer Res. (1982) 42:849-855; Mazauric et al., Cancer Res. (1982) 42:150-154; Varki et al., 44:2052-2061. A few antibodies have been reported to be specific for one of the subtypes of lung cancer: small cell lung cancer (Bell and Seetharam, Int. J. Cancer (1976) 18:605-611; and oat cell tumor (Bernal and Speak, Cancer Res. (1984) 44:265-270. See also, DeSchryver-Keckemetri et al., Lab. Invest. (1979) 41:432-436 and Veltri et al., Br. J. Cancer (1980) 41:705-715.

Several different tumor-associated antigens expressed by non-lung cancer cells have previously been described as glycoconjugants. See, Hakomori and Kannagi, J. Nat. Cancer Inst. (1983) 71:231-251; Feizi (1984), in Genes and Antigens in Cancer Cells—The Monoclonal Antibody Approach; Contributions to Oncology, Vol. 19, Reithmuller et al., eds. (Kager, Basel) pp. 51-63; Ginsburg et al., ibid., pp. 51-63; Dippold et al., Proc. Natl. Acad. Sci. USA (1980) 77:6114-6118; Bumol and Reisfeld, ibid. (1982) 79:1245-1249; Hellstrom et al. in Genes and Antigens in Cancer Cells—The Monoclonal Anti-body Approach; Contributions to Oncology, Vol. 19, Reithmuller et al., eds. (Kager, Basel) pp. 121-131; and Atkinson et al., Cancer Res. (1982) 4820-4823.

SUMMARY OF THE INVENTION

A carbohydrate antigenic epitope is detected in glycoproteins associated with squamous lung carcinomas and in human hosts having squamous lung carcinomas. Specific antibodies are provided for detecting the presence of the epitope. The antigens and/or antibodies may find use in vitro or in vivo in diagnosis and therapy. Antiidiotypic antibodies may also find use for detecting the presence of antibodies to the antigen in the blood or serum of a human host, as well as use as antigens.

DESCRIPTION OF THE SPECIFIC EMBODIMENTS

Compounds are provided which include at least in part a polysaccharidic epitope which serves as a marker for squamous lung carcinoma (SLC). The epitope may be found on cells in biopsies in blood of humans having SLC, in lysates of tissue or transformed cells in culture or other cells associated with SLC. The antigen may be part of a glycoprotein or a polysaccharide substantially free of polypeptide.

Growing SLC cells in vitro in appropriate culture medium, provides a group of glycoproteins having the same epitopic site in being recognized by the same monoclonal antibody. The glycoproteins in the supernatant from the cell culture vary over a large molecular weight range, varying from about 50kDal (kiloDaltons) to about 1mDal (megaDaltons) or more, with a substantial fraction of the glycoproteins being in the range of about 50 to 200kDal.

The subject glycoproteins are almost totally bound by wheat germ lectin and can be eluted with 0.1M N-acetylglucosamine and partially bound by concanavalin A (con A) and eluted with methyl-$\alpha$glucopyranoside. Furthermore, the amount of the subject glycoprotein which binds to the wheat germ lectin will range from about 30-40% of the total glycoprotein released into the medium by SLC cells.

The subject glycoproteins are solubilized by Triton X-100 non-ionic detergent from SLC cells in culture and those glycoproteins spontaneously released into the media, show broad distributions of electrophoretic mobilities. Although individual bands of apparently discrete structure are seen in both distributions, no bands are clearly resolved in electrophoresis and the positions of major bands do not correspond to these positions as determined by immunoblot.

Serum samples from SLC patients are found to have the subject glycoproteins or saccharides in blood, which components bind to specific antibodies. By contrast, healthy individuals and individuals having other types of cancer are substantially free of compounds having the same epitopic site.

Upon denaturation of the glycoproteins released by SLC cells followed by protease hydrolysis, e.g., protease K, carbohydrate chains in exclusion column chromatography are eluted in a molecular weight region of less than that of an ovalbumin marker (45kDal), although some portion of the carbohydrate composition elutes, where the exclusion is about 250kDal. Digestion with endoglycosidase F, a glycosidase cleaving both complex and high mannose type glycans near their asparagine attachment sites in glycoproteins, produces carbohydrate chains having about the same size as those obtained after hydrolysis of the glycoproteins with protease K, including the large carbohydrates. There is no apparent effect of the endoglycosidase F on the antigenicity of the carbohydrate antigen. The subject epitope does not cross react with most tested blood group antigens as evidenced by direct and indirect agglutination and by dot-blot analysis on solubilized membrane preparations. Furthermore, it appears that binding of the antibody to the epitopic site, when present on intact cells, results in endocytosis of the antibody.

The antigens carrying the subject epitope may be isolated from either or both SLC cells or supernatant medum in which the cells are grown. The supernatant medium may be separated from the cells, insoluble material and cell debris removed, e.g., by centrifugation, and the glycoproteins precipitated at reduced temperatures employing ammonium sulfate. The ammonium sulfate concentration is raised to about 75% w/v final concentration. The precipitates may then be collected and further purified employing gel permeation columns, e.g., Sephacryl SX00 (X=2-4) columns. The bulk of the glycoproteins elute with the void volume, with S200, S300 and S400 columns. The equilibrating and eluting solution is conveniently phosphate buffered saline plus a small amount of a non-ionic detergent, usually about 0.01 to 0.2%, e.g., 0.1% Tween 20.

The glycoprotein fraction may be used in accordance with conventional ways to immunize a mammal, e.g., mouse or higher mammal, e.g., primate, including human in accordance with conventional procedures. See for example, EPO Publ. No. 0 044 722 and U.S. Pat. Nos. 4,172,124; 4,350,683; 4,361,549; and 4,464,465. Hybridomas may be prepared by fusing available myeloma lines, e.g., NS/1, Ag8.6.5.3, etc., with peripheral blood lymphocytes, e.g., splenocytes or other lymphocytes of the immunized host and the resulting immortalized B-lymphocytes, e.g., hybridomas, heteromyelomas, EBV transformed cells, etc., selected, cloned and screened for binding to the subject epitope.

Once antibodies are available which are specific for the epitope, the antibodies may be used for the screening. Thus, by emploring the subject antibody 43-9F Mab (monoclonal antibody) or antibodies prepared to the epitope which cross react with 43- 9F Mab, one can rapidly screen for different antibodies, from the same or different host, binding to the same epitope. Monoclonal antibody 43-9F is secreted by hybridoma cell line ECACC No. 85013101 deposited on Jan. 31, 1985 with the PHLS Centre for Applied Microbiology and Research, of the European Collection of Animal Cell Cultures (ECACC), Porton Down, Salisbury, Wiltshire, SP4 OJG, United Kingdom.

The antibodies obtained and employed may be any one of the classes, such as IgA, IgD, IgE, IgG and IgM, and any one of the subclasses of the various classes. In addition, whole antibodies or fragments of the antibodies may be employed, such as Fab, $F(ab)'_2$, $F_v$, or the like. The subject immortalized B-lymphocytes or other cells, e.g., T-cells, which provide receptors specific for the subject epitope, may be used as a source of DNA, either genomic or cDNA, for expression of the light and heavy chains of the receptors in prokaryotes or eukaryotes. The resulting products may then be used as receptors for binding to the subject epitopes.

The polysaccharide epitopes may be characterized as being present in glycoproteins released by human lung cancer cells, which polysaccharide binds specifically to the monoclonal antibody 43-9F and is of less than about 250 kDal, generally less than about 45 kDal.

Monoclonal antibodies may be used in other ways than binding to the subject epitope site. Monoclonal antibodies to the epitopic site may in turn be used as antigens for the production of monoclonal antibodies specific for the idiotypic site of the Mab to the glycoprotein ($Mab_{gp}$), e.g., 43- 9F. The antiidiotypic monoclonal antibody ($Mab_{id}$) may be used to detect the presence of antibodies in a host to the glycoprotein, where the $Mab_{gp}$ and physiological fluid to be diagnosed are from the same host. For example, where the $Mab_{gp}$ is a human antibody ($hMab_{gp}$), then the $hMab_{gp}$ may be used as an antigen to make monoclonal ant specific for the human idiotype for the glycoprotein, which monoclonal antibodies could be used to detect antibodies to the glycoprotein which may be present in a human physiological fluid, e.g., blood or serum. The $Mab_{id}$ may be made in any host, e.g., rodent, more particularly, mouse.

In addition, the conformation of the idiotype of the $Mab_{id}$ will resemble the epitope of the glycoprotein and thus may serve as an antigen in competition with the glycoprotein epitope. To that extent, the $Mab_{id}$ may serve as a vaccine in inducing an immune response to the glycoprotein epitope different from the immune response obtained with the glycoprotein. Furthermore, the $Mab_{id}$ may serve as a reagent as a ligand to be competitive with the glycoprotein.

The antibodies may find use in diagnosis, with tissue employing cytology, with lysates of tissue or in detecting the subject epitope in blood or serum. A wide variety of techniques and protocols exist for detecting an antigen in a sample suspected of containing the antigen. Protocols involve a wide variety of labels, which labels include radionuclides, enzymes, fluorescers, fluorescer-quencher combinations, chemiluminescers, magnetic particles, and the like. These labels may be directly conjugated to the monoclonal antibody through a variety of covalently bonded linking groups and functionalities. Some of the techniques involve having one of the members of the antigen-antibody complex bound to a support, such as a particle or vessel wall, while other of the assays are performed in solution without a separation step, where uncomplexed label is separated from complexed label. In a number of assays, the antibody need not be labeled, such as in hemagglutination or where anti-immunoglobulin is employed and the anti-immunoglobulin is labeled, so as to provide for indirect labeling of the subjet monoclonal antibody. Assays which may be employed include such assays as dot blot, ELISA, RIA, EIA, etc.

For high sensitivity, the dot blot assay appears to have advantages, being able to detect the amount of epitope of a single cell. Therefore, this assay is preferred for biopsies for detecting the presence of SLC cells in tissue. The soluble proteins may be separated from nuclei and cell debris and crude extracts or partially purified proteins bound to a support, e.g., nitrocellulose. The presence of the subject epitope may then be determined employing antibodies which are labeled or employing anti-immunoglobulin to the antibodies to the subject epitope in a two-step procedure.

The subject antibodies may also find use for imaging and therapy in vivo. Depending upon the level of the subject antigens in the blood stream, the subject antibodies may be introduced into the blood stream for transport to sites where subject antigens exist, indicative of the presence of SLC. Various labels may be employed, such as radionuclides, e.g., technecium, rhenium, iodine, copper, indium, nmr additives, toxins, etc.

The following examples are offered by way of illustration and not by way of limitation.

EXPERIMENTAL

The following abbreviations are employed:

FCS—fetal calf serum

PMSF—phenylmethylsulfonyl fluoride

PBS—phosphate buffered saline

BSA—bovine serum albumin
FACS—fluorescence activated cell sorter
FITC—fluoresceinisothiocyanate
EDTA—ethylenediaminetetracetic acid
PEG—polyethylene glycol
HAT—hypoxanthine-aminopterin-thymidine
ELISA—enzyme linked immunosorbent assay

Cells and Cell Culture

Human squamous lung carcinoma line RH-SLC-11 (described in Olsson et al., *Cancer* (1984) 1757-1765) was cultivated in RPMI-1640 medium plus fetal calf serum (RPMI/FCS). The cells are routinely grown attached in plastic vessels. They can also grow in serum-free RPMI-1640 medium for periods up to 7 days with growth rates only slightly less than that in serum containing media. A human small cell lung carcinoma line RH-SCC-L10 was similarly maintained. The human cancer cell line V-266, a human myeloma line, 1-11D, and a hybridoma from human lymphocyte fusion with RH-L4 (B-lymphoma, Olsson, et al., *J. Immunol. Methods* (1983) 61:17-32) were also grown in RPMI/FCS as were also the promyelocytic HL-60 leukemia cell line (Gallagher et al., *Blood* (1979) 713-733), U937 histiocytic lymphoma cell line (Sundstrom and Nilsson, *Int. J. Cancer* (1976) 565-577), RH-L4 B-lymphoma cell line (Olsson et al., 1983, supra), and foreskin fibroblasts. Normal human mononuclear leucocytes and erythrocytes were isolated as described previously (Olsson et al., *J. Immunol. Methods* (1983) 61:17-32). Normal human lung cell populations were obtained from patients that underwent lobectomy of the lung for reasons other than malignant disease. The biopsies for analysis included a piece of bronchus.

Tumor Specimens and Serum Analysis

Tumor specimens were obtained as fresh biopsy material from patients with a variety of malignant diseases. Most of the material was homogenized after isolation of the cortical part of the tumor that normally contains most of the tumor cells, frozen in RPMI-1640 containing 30% FCS with 10% dimethyl sulfoxide (DMSO), and stored in liquid nitrogen. The leukemia samples were obtained from fresh marrow aspirates. Serum samples from cancer patients were obtained at the time of diagnosis. Serum samples from healthy persons were obtained from blood donors at blood banks.

Purification of Glycoproteins Released by SLC Cells

The RH-SLC-L11 cells were grown in 150cm$^2$ or 300cm$^2$ plastic dishes at 37° C. in 5% CO$_2$ atmosphere in RPMI 1640 media minus serum at cell densities at least 2×10$^4$ cells per ml media. After 4-5 days of growth, the medium was withdrawn, chilled to 4° C. and centrifuged at 30,000 g for 20min to remove cell debris or other insoluble material. A solution of saturated ammonium sulfate (Sigma Grade VI) was added slowly with continuous mixing to provide a 75% w/v final concentration, and stirred overnight at 4° C. The amount of media processed at a single time varied from 100 ml to 1.5L. Precipitates were collected by centrifuging 30,000 g for 30min and resuspended in a small volume of 0.1M Na phosphate, pH=7.0, at a protein concentration of about 2 to 5 mg/ml. Protein concentrations were estimated from UV absorption assuming a 1.0 mg/ml solution has O.D.$_{280}$=1.0 Parts or all of the preparation were then applied to Sephacryl S200, S300, or S400 columns (Pharmacia) (25cm×0.8cm$^2$) equilibrated with phosphate buffered saline (PBS) or with PBS plus 0.1% Tween 20 and the column was eluted with the same solution at a flow rate of 20 ml/hr. The bulk of the glycoproteins and 43- 9F antigen eluted with the void volume. Recovery of glycoprotein was nearly 100% when the Tween was included in solutions but was usually less than 30% of applied material without Tween. After degradation with protease K, carbohydrates were quantitatively recovered with or without Tween. To prepare $^3$H-labeled glycoproteins, the RH-SLC-L11 cells were grown for the last 2 days in serum-free RPMI 1640 media in the presence of [$^3$H]-glycosamine (Amersham) 3-10 μCi/ml, 3.5 Ci/mmole. The media was collected and labeled glycoproteins purified as just described above.

Purification of Carbohydrates from Glycoproteins

The glycoproteins released by RH-SLC-L11 cells, purified as described above, were boiled 2 min in a solution containing 0.10M Na phosphate, pH 7.0, plus 0.10% SDS and chilled. The solution was diluted 4 fold with the same phosphate buffer to give a protein concentration of 200-300 μg/ml and protease K (Boehringer Mannheim, autodigested 2hr at room temperature) was added to a final concentration of 375 μg/ml. This was incubated 16-18hr at 37° C., then additional protease K was added to a final concentration of 750 μg/ml and incubation continued for 2-3hr. The solution was boiled 10 min, cooled and applied to a Sephacryl S200 column (25cm×0.8 cm$^2$, excluded protein mol wt=250kDal) and eluted at a flow rate of 20 ml/hr to separate smaller chain carbohydrates from those eluting at or near the void volume.

Antibodies

The 43- 9F antibody (IgM) was secreted by a mouse hybridoma obtained as follows. Balb/c mice were immunized with 3 injections of 5×10$^6$ RH-SLC-L11 cells per injection at day 0, day 14 and day 21; the first two injections intraperitoneally, the last intravenously. Mononuclear spleen cells were isolated 4 days after the last immunization and fused with the non-producer X63-Ag8.6.5.3 mouse myeloma line in PEG (37%; 1kDal) at room temperature. The cells were seeded in 96-well plates in RPMI-1640 with 15%FCS immediately after fusion. Twenty-four to 48 hr later, the medium was exchanged with selective HAT medium with 15% FCS and grown in this medium for 14 days with medium renewal every 3 to 4 days. The supernatants were tested for their content of immunoglobulin by ELISA and the specificity for cell surface antigens by cell-binding ELISA and analysis in FACS 14 to 30 days after fusion. Hybridomas of interest were cloned by limiting dilution in HAT medium with murine thymocytes as feeder cells. Cloned hybridomas were expanded in mice as ascites tumors. Monoclonality of the hybridoma cultures was assessed by SDS analysis of $^{35}$S-methionine labeled Ig products and the isotype of the immunoglobulin determined by titration against isotype specific antibodies. For further details, see Olsson et al., *Cancer* (1984) 54:1757-1765, which is incorporated herein by reference.

Ascites fluid was partially purified by passing through a 100cm×30cm$^2$ S300 Sephacryl column and collecting fractions from the void volume. The most highly purified antibody was prepared from supernatant obtained from serum-free HB102 media (Hanna Biologicals, California) in which the 43- 9F hybridoma was grown. The IgM was precipitated from the media with 50% w/v ammonium sulfate and applied to Sephacryl S300 column equilibrated with PBS. Fractions from the void volume contained IgM contaminated with only trace amounts (<0.5%) of two other proteins detectable by Coomasie blue staining after electrophoresis on 10% polyacrylamide gels.

Labeling with $^{125}$I

Glycoproteins and antibodies were labeled either via lactoperoxidase coupled to beads (Biorad) or using the IodoGen (Pierce) reagent (Fraker and Speck, *Biochem. Biophys. Res. Commun.* (1978) 80:849–857). Labeled proteins were separated from free iodine by centrifugation through a small S25 Sephadx column mounted in a centrifuge tube to catch the flow through containing labeled proteins. Specific activity of antibodies was generally in the range $0.5$–$2\times10$ cpm/$\mu$g to avoid multiple labeled molecules. The amount of labeled antibody able to recognize antigen was estimated by applying the antibody to an affinity column (Affigel-Biorad) in which total proteins in a Triton X-100 lysate of RH-SLC-11 cells were conjugated.

Cell Lysis and Dot-blot Analysis

Cell extracts or purified proteins were analyzed for binding of antibodies in a dot blot assay with antigen attached to nitrocellulose sheets (Biorad). Cultured cancer or normal cells were collected from their growth media by centrifugation, washed in PBS and then washed and resuspended in a solution containing 0.02M Tris pH 7.5, 0.02M NaCl 0.2mM PMSF, 0.10M sucrose, at a concentration of $1\times10^7$ to $1\times10^8$ cells/ml. These cells had been scraped loose from plastic dishes with a rubber policeman. Cells were disrupted in the presence of 1.0% Triton X-100 in a Potter-Everhjem homogenizer and soluble proteins separated from nuclei and cell debris (Lydersen & Pettijohn, *Cell* (1980) 489–499). Protein concentration in the cell-free extract was determined in an acidic Coomasie brilliant blue solution (Sedmak and Grossberg, *Anal. Biochem.* (1977) 79:544–552). Crude extracts or partially purified proteins were applied to nitrocellulose by absorbing a measured sample of 2 to 5$\mu$l directly with a micropipette and allowing the sample to air dry. The sheet was then washed in an agitation tray with 2 changes of PBS solution containing 0.05% Tween. Some of the applied protein usually washed off at this time. Measured by retained $^3$H-radioactivity, the [$^3$H]-glycoproteins purified from media were irreversibly bound to an extent of 20–25%, when applied as described at a concentration of approximately 500$\mu$g/ml or less. The sheets were then incubated in sealed plastic bags with either $^{125}$I-labeled antibody ($1$–$2\times10^6$ cpm per 100 cm: nitrocellulose) or unlabeled antibody (4 $\mu$g/ml purified IgM) in PBS solution containing 30% FCS plus 0.05% Tween. After 2 hr incubation at room temperature in a shaker, the nitrocellulose was removed and washed in PBS-Tween solution.

When radiolabeled antibody was used, the washing was extended over a 6–12 hr period with 4–5 changes; the sheet was then dried and applied in a plastic envelope to Kodak X-ray film at $-60°$ C. to obtain an autoradiogram of the dot blots. When unlabeled monoclonal antibody was used, it was detected by incubating the washed sheet with a 1:500 dilution of a peroxidase conjugated rabbit-anti-mouse IgG light chain (DAKO) in PBS Tween plus 30% FCS. After washing the sheet, the peroxidase staining was developed with diaminobenzidine.

To estimate the relative amount of $^{125}$I-labeled antibody bound in dot blots, autoradiograms were scanned with a Zeiss recording microdensitometer and integrated via a Brock and Michelsen digital processor. Calibrations were made by scanning autoradiograms of known amounts of $^{125}$I-Mab. These showed that a linear relationship between integrated areas and bound Mab existed over a limited range. Although autoradiographic exposures were adjusted to avoid the non-linear region, this was not always convenient and in some of the assays maximal radioactivities in certain dot blots are underestimated relative to blots of lesser radioactivity on the same autoradiogram. However, this possible source of error does not influence the determination of elution points in column chromatography or of the points of maximal dot blot reactions in kinetic studies.

Immunoblot and Polyacrylamide Gel Electrophoresis

Conditions for SDS-polyacrylamide gel electrophoresis, electrophoretic transfer of proteins to nitrocellulose sheets and immunoblotting were described previously (Van Ness and Pettijohn, *J. Mol. Biol.* (1983) 171:175–205). To analyze proteins previously separated by electrophoresis, bands were cut from Coomasie blue stained gels with a razor blade. The gel slice was crushed, soaked in sample buffer solution containing 10% glycerol and introduced into a well of a fresh polyacrylamide gel for re-electrophoresis.

Solid Phase Radioimmune Assay

Purified glycoproteins released from RH-SLC-L11 cells were coated onto wells of Linbro disposable 96 well microtiter dishes (Flow Laboratories) by incubating 16hr at room temperature with 50 $\mu$l per well of PBS containing a constant amount of protein (10–50 $\mu$g depending on the experiment). The wells had previously been coated with poly-L-lysine (10 $\mu$g/ml) by incubating overnight. The dishes were washed with 4 changes of a solution containing PBS 0.05% Tween and incubated 1–2 hr with PBS containing 1% FCS. After removing this solution it was replaced with 50 $\mu$l per well of a PBS solution containing 1% FCS, plus constant amounts of $^{125}$I-labeled 43-9F antibody (5 to 50 ng) and variable amounts of carbohydrate or glycoprotein competitors. After 5 hr incubation at room temperature, the radioactive solutions were removed, the wells were washed 5 times with PBS-Tween, individual wells were cut out and counted in a gamma counter. Identical samples in triplicate were used and results expressed as averages. The amount of antibody bound in the absence of a competitor was generally in the range 20 to 50% of that able to bind antigen, the amount being estimated as described above. Several wells in each plate were not coated with glycoproteins but were otherwise identically processed. Radioactivity binding to these served as background controls which usually amounted to 5–10% the amount bound to antigen coated wells in the absence of competitor; this background was subtracted from all measurements of bound antibody.

Enzyme-linked Immunosorbent Assay (ELISA)

For testing reactivity of tumor cells with the 43-9F antibody by ELISA methods, Triton X-100 extracts were prepared from tumors and wells of 96 well plates coated with extract corresponding to roughly $10^5$–$10^6$ cells, as described above. The monoclonal 43-9F antibody was peroxidase conjugated and the ELISA assay carried out as a one-step procedure. The plates were incubated with the specific antibody (~100ng/well) for 1 hr at 20° C. and 1 hr at 37° C., washed in PBS/Tween, and incubated with substrate as described by Kennett (1980) in: *Monoclonal Antibodies,* Kennett et al., eds., Plenum Press, N.Y., pp. 376–377, and read after 15 min and 45 min on an automatic Titertek micretiter well plate scanner. The values at 45 min were used. Optical density (O.D.) for background values were <0.200; weak (+) reactions were O.D. 0.2–0.4; strong (++) and very strong (+++) reactions were O.D. 0.4–0.8 and >0.8, respectively. Some analyses were done in parallel with the 43- 9F Mab both as matching and detecting antibody. However, the latter type of ELISA was not superior to the one-step procedure described above. In contrast, the sandwich ELISA assay was used for analysis of antigen in serum. The one-step procedure could not be used in this case, because the seral proteins compete for attachment of the specific antigens to plastic. The assay was therefore done as a sandwich assay in which the plates are coated with unlabeled 43- 9F antibody (1 μg/ml, 100 ng/well), washed in PBS/Tween, blocked with PBS/1% BSA, incubated with serum diluted 1:1 in PBS for 1 hr at room temperature and 1 hr at 37° C., washed, and incubated for 2 hr at room temperature with peroxidase conjugated 43- 9F. The reading of the test was done as described above.

Electron Microscopy

The procedure for processing of adherent, cultured cells for electron microscopy are as follows. Culture medium was decanted and replaced by 2% glutaraldehyde in 0.1M cacodylate buffer at pH 7, and the culture left at room temperature overnight. Subsequently, the cells were osmicated in situ for 1 hr, rinsed in distilled water, treated for 30 min with 1% aqueous uranyl acetate, rinsed in distilled water, and dehydrated in graded ethanol up to 90% ethanol. Dehydration was then continued in hydroxypropyl methacrylate, followed by infiltration with hydroxypropyl methacrylate-Epon mixtures to pure Epon. The cells were sectioned parallel to or perpendicular to the plane of the culture. The sections were contrasted with lead citrate.

RESULTS

Derivation of Specific Mabs

Mice were immunized with RH-SCL-L11 or RH-SCC-L10 cells and their spleen cells subsequently fused with a HAT-sensitive mouse myeloma cell line (X63-Ag8.6.5.3). Hybridoma supernatants were screened for reactivity to the lung tumor cells by cell-binding ELISA (Olsson, *Cancer Metastasis Rev.* (1983) 2:153–163)

EL and by FACS. For the latter analysis, cells were stained in a two-step procedure with hybridoma supernatant as a first step and FITC-conjugated rabbit anti-mouse Ig (Dako, Denmark) as a second step. Mab reactive with the lung tumor cell line was subsequently tested against a panel of normal and neoplastic human cells, including lymphocytes, granulocytes, monocytes, erythrocytes, thymocytes, bone marrow cells, fibroblasts, lung tissue, leukemia cells, lymphoma cells, myeloma cells, carcinoma cells and melanoma cells. Three Mabs, designated 2-4D, 2-9F, and 3-5B, reacted with lung tumor cells, but none with any of the other cell types. These antibodies were therefore assumed to detect lung tumor-associated antigens. These three were cloned by limiting dilution and subsequently tested for binding to 11 subclones of the RH-SLC-L11 cell line. One of these Mabs (designated 43- 9F; IgM) was found to bind to all subclones and was consequently used for all subsequent studies.

Dot-blot Analysis

Procedures using dot blots were devised to assay the antigen recognized by the 43- 9F antibody.

Triton X-100 extracts of cell suspensions ($1 \times 10^7$ to cells/ml depending on cell volume) were prepared, the protein concentration of each cell free extract determined and 5 μl samples of dilutions of the extracts absorbed on a nitrocellulose sheet. After blocking non-specific absorption sites the sheet was incubated with $2 \times 10^6$ cpm of 1:160 $^{125}$I-labeled 43- 9F antibody (specific activity about $2 \times 10^6$ cpm/μg), washed, dried and exposed to Kodak X-ray film. An identical analysis was also carried out except that a 100-fold excess of non-radioactive 43- 9F antibody was included with the $^{125}$I-antibody. The 43- 9F antigen was readily detected in extracts of two cloned cell lines of different squamous lung carcinomas, whereas specific binding could not be detected in extracts from normal human cell types or other cancer cell lines. The 43- 9F negative cell types include those derived from other types of human lung cancer cells, from normal lung cells as well as cell lines derived from malignant neoplasms of other tissues and some other normal tissues. Faint positive reactions were occasionally seen with undiluted extracts of cell types other than squamous lung carcinomas, but these reactions were attributed to weak non-specific binding of the 43- 9F antibody, since they were not competed by excess of the 43- 9F antibody, unlike the specific reaction.

For example, the weak reaction of $^{125}$I-labeled 43- 9F antibody with proteins from L4 lymphoma cells was only moderately diminished by including 100-fold excess of unlabeled 43- 9F antibody, while binding to antigens in the squamous lung carcinoma extracts was significantly reduced. Extracts from most cell types (other than RH-SLC-cells) were completely negative for reaction with the 43- 9F-antibody. For example, normal lung tissue or small cell carcinoma cells gave no detectable reaction and quantitative comparison of the dot blots permitted the estimation that the amount of 43- 9F antigen in these extracts is <0.02% of the amount seen in the RH-SLC-L11 line. The normal lung tissue included bronchi and therefore also normal squamous cells, indicating that the 43- 9F antigen is undetected in that cell type, a finding also supported by analysis of mucosal squamous cells.

Using an ELISA assay, the 43- 9F antibody was found to be highly specific for squamous lung cancer, and although an occasional isolated specimen from other tumor types did show weak reactivity with the 43- 9F antibody, only squamous lung carcinomas were strongly positive.

The dot-blot analysis is a significantly more sensitive and reliable assay than ELISA. Calculations from the number of cells used to prepare the cellular extract for dot blot indicate that the sensitivity of the assay is sufficient to detect amounts of antigen less than that present in one cell. The dot-blot assay seems superior to other available methods to detect minute amounts of tumor cells in otherwise normal tissues and could be useful to detect micrometastatic lesions.

The 43-9F Antigen is Released from Cells in vitro

Large amounts of [$^3$H]-glucosamine labeled, soluble-glycoproteins can be detected in the culture medium of growing RH-SLC-L11 cells. The amount is not significantly different from that observed with other lung tumor cells such as small cell lung carcinomas. Dot-blot analysis revealed that the 43-9F epitope is present on at least a portion of the molecules released by RH-SLC cells, but not on those released by other cell lines. The rate of release of the antigen and of total [$^3$H]glycoproteins was similar, when the cells were grown with or without fetal calf serum. When RH-SLC-L11 cells were labeled with $^3$H-glucosamine and then transferred to non-radioactive media, the initial rate of appearance of labeled macromolecules in the media was indistinguishable from that occurring in a similar culture containing sodium azide and cycloheximide to block metabolism. These rates were similar to that in the continuously labeled culture for nearly 24 hr. Most of the metabolically blocked cells were non-viable (assayed by trypan dye-exclusion) by this time. Release rates of the 43-9F antigen, estimated by dot-blot assay, were also similar in the metabolically blocked cells and in normally growing cells for many hours and then declined in the non-growing cells. After 24 hr, the absolute amount of soluble antigen in the culture medium with inhibitors began to decrease. This is attributable to degrading enzymes in the media coming from the decaying cells. However, the major proportion of released glycoproteins and the 43-9F antigen are not derived from decaying cells, since populations of dying or dead cells do not show enhanced rates of release. These results show that release of antigen and total glycoproteins can be a spontaneous solubilization without evidence of an active secretory process. The pool of [$^3$H]-labeled glycoproteins to be shed is apparently large, since the release reate from labeled cells growing without [$^3$H]-glucosamine is comparable for many hours to that of the cells growing with the labeled glucosamine. Indeed, the results show that the released glycoproteins account for a major fraction (~85% of the total incorporated [$^3$H]-labeled glucosamine of the RH-SLC cells. The RH-SLC-L11 cells can be grown in vitro in RPMI-1640 medium without serum supplements, and released macromolecules binding the 43-9F antibody can be readily prepared from this media in substantially pure form.

43-9F Epitope is Present on a Diverse Group of Glycoproteins

The molecules released from RH-SLC-L11 cells were applied to lectin affinity columns. Proteins shared by RH-SLC-L11 cells were concentrated by ammonium sulfate precipitation, suspended in 0.02M Na phosphate, pH=7.0, and applied to a 1.0 ml column of Sepharose conjugated to con A or wheat germ lectin. After four reapplications of the column flowthrough, the column was washed with 0.02M Na phosphate and specifically bound molecules eluted with 0.1M N-acetyl glucosamine (wheat germ lectin) or 0.3M methyl-$\alpha$-pyranoside (con A). Samples (5$\mu$l) of the applied proteins, the column flowthrough and wash fractions, and the eluted fractions were absorbed on a nitrocellulose sheet and analyzed for 43-9F antigen using $^{125}$I-(43-9F)-antibody. A dot-blot analysis was employed as described previously. The immunoblot analysis of 43-9F antigen was performed after polyacrylamide gel electrophoresis. Proteins in Triton X-100 extracts of RH-SLC-L11 cells or in purified release proteins were heated to 100° C. in SDS solution containing $\beta$-mercaptoethanol, separated by electrophoresis on an SDS 10% polyacrylamide gel and then transferred electrophoretically to a nitrocellulose sheet. The nitrocellulose sheet was subsequently probed with $^{125}$I-labeled 43-9F antibody ad an autoradiogram of the dried sheet obtained. The wheat germ lectin retained nearly all of the 43-9F antigen detectable by dot-blot assay and the antigen could be eluted by 0.1M N-acetylglucosamine. Thus, the molecules recognized by the 43-9F antibody appear to be glycoconjugates. Part of the applied antigen was also retained on a con A column and could be eluted with methyl-$\beta$-glucopyranoside, which supports the interpretation of the antigen being a glycoconjugate. Further studies showed that when all detectable 43-9F antigen was bound to a wheat germ lectin column, only about 36% of the total radiolabeled compounds released by RH-SLC-L11 cells was bound. Thus, it seems that the epitope recognized by the 43-9F antibody is present on only part of the molecules released into media by the RH-SLC cells.

Immunoblot analysis (Western blot) demonstrated that after reduction and denaturation in SDS, molecules recognized by the 43-9F antibody have diverse electrophoretic mobilities spanning an equivalent protein $M_r$ in a range of 50,000–300,000. Larger molecules were not accommodated by the gel.

Proteins from other (non-RH-SLC) cell types have no reacting components in the immunoblot analysis. The apparent disperse size range of the antigen is not attributable to artifacts in electrophoresis, since antigens of discrete sizes eluted from a gel slice of a previous electrophoresis, re-ran true, and generated narrow bands characteristic of near homogeneous species. The different sized antigens from the cell extract were not produced by proteolytic degradation, since the relative number of molecules having high or low electrophoretic mobilities identified either by protein staining or by immunoblotting did not change after extended incubation or extracts. When the preparations from SLC cells were incubated with protease K prior to electrophoresis all reacting components in the immunoblot assay were lost. Controls incubated without the protease were not affected. It follows that the molecules recognized by 43-9F antibody involve proteins.

The total 43-9F antigens solubilized with Triton X-100 from RH-SLC-L11 cells and also those spontaneously released into media showed broad distributions of electrophoretic mobilities. Although individual bands of apparently discrete structure were seen in both distributions, no bands were clearly resolved and the positions of the major bands in the adjacent immunoblot did not correspond. Coomasie blue staining of a similar gel indicated that the major stained released protein barely entered the running gel and had a molecular weight significantly greater than the 200kDal marker. A partly resolved band at this position was also seen in the corresponding immunoblot, but many other species of smaller sizes having near continuous electrophoretic mobilities were also evident. The immunoblot and lectin affinity analyses indicate that the molecules recognized by the 43-9F antibody are a diverse set of primarily large glycoproteins.

Detection of 43-9F Antigen in Serum

Serum samples from 109 lung cancer patients were obtained at the time of diagnosis, and analyzed for reactivity with 43-9F antibody. In addition, serum samples from 144 patients with other types of cancer were analyzed as well as serum from 1910 apparently healthy individuals.

TABLE 1

Analysis of the 43-9F antigen in serum from lung cancer patients, and from healthy persons.

| Patient Category | # Samples (patients) | # Positive + | # Positive ++ | # Positive +++ | Total # Positive/ Total # |
|---|---|---|---|---|---|
| Lung Cancer: | | | | | |
| Squamous | 76 | 3 | 49 | 8 | 60/76 |
| Small Cell | 20 | 0 | 0 | 0 | 0/20 |
| Adenocarcinomas | 9 | 1 | 0 | 0 | 1/9 |
| Others | 4 | 0 | 0 | 0 | 0/4 |
| Other cancers: | | | | | |
| Gastrointestinal | 54 | 2 | 0 | 0 | 2/54 |
| Breast | 41 | 2 | 1 | 0 | 3/41 |
| Bladder | 35 | 1 | 0 | 0 | 1/35 |
| Ovarian | 32 | 1 | 2 | 0 | 3/32 |
| Sarcomas | 19 | 1 | 0 | 0 | 1/19 |
| Leukemias | 17 | 1 | 0 | 0 | 1/17 |
| Healthy Persons: | 1910 | 18 | 1 | 0 | 19/1910 |

ELISA reactions were done as described in Experimental Section.

As listed in Table 1 about 80% of the patients with squamous lung carcinoma were positive at the time of diagnosis, whereas the percentage of positive cases in other types of cancers were ~6%, and in the healthy control group ~1%.

Properties of the Secreted 43-9F Antigen

Exclusion chromatography of glycoproteins released from RH-SLC-L11 cells were performed as follows. Proteins unlabeled or labeled with [$^3$H]-glycosamine were prepared from culture media by ammonium sulfate precipitation and desalted on a G25 Sephadex column. After incubation with different enzymes, portions were applied to the same S200 Sephacryl column (25cm×0.8 cm$^2$, excluded protein mol. wt.=250,000) and eluted at a flowrate of 20 ml/hr. The fractions were monitored by absorbance. In a second study, [$^3$H]-glucosamine labeled glycoprotein (about 20 μg protein) was boiled in a solution containing 0.10% SDS, 0.02M NaCl, 0.02M Na phosphate, pH=7.0, and then incubated 16 hr at 37° C. in a solution containing either no further additions or 800 μg/ml protease. Dot-blot analyses were made of the proteins after incubation. In the third study, the [$^3$H]-glucosamine labeled glycoproteins (as described above) were boiled in a solution containing 0.1% SDS, 0.05% Non-idet P-20, 0.1% Triton X-100, 10mM EDTA, Na borate buffer, pH=6.1, cooled and incubated 16 hr at 37° C. with or without 4 units purified endoglycosidase F (endo F) (protease free). Dot-blot analyses were employed again.

An analysis using exclusion column chromatography of the glycoproteins and the 43-9F antigen released by RH-SLC-L11 cells showed that the bulk of the UV absorbing components as well as nearly all of the [$^3$H]-glycosamine labeled components were excluded on Sephacryl S-200, indicating a $M_r$>200kDal. Likewise, the 43-9F antigen assayed by the dot blot method eluted primarily in the void volume with a profile resembling that of the total glycoproteins. There were however minor components retarded on the column in the approximate $M_r$ range 50,000–200,000Dal. When the glycoproteins were denatured in SDS solution and then hydrolyzed exhaustively with protease K, $^3$H-labeled carbohydrate chains eluting in a molecular weight region less than that of an ovalbumin marker (45,000Dal) were liberated. However, part of the labeled carbohydrate chains maintained very large sizes eluting at or near the void volume.

In the next study, exclusion chromatography of 43-9F antigen on a Sephacryl S-400 column was performed. RH-SLC-L11 cells were grown for 4 days with [$^3$H]-glucosamine, a Triton X-100 lysate of the cells made, and the lysate centrifuged to eliminate cell debris. To 0.2 ml of the supernatant SDS was added (final concentration, 0.3%) and the mixture boiled for 5 min, cooled and applied to a Sephacryl S-400 column.

When the proteins were labeled to high specific activity with $^{125}$I, then degraded with $^{125}$I-labeled peptide fragments eluted near the included volume at the position of a thymidine marker; none could be detected in the void volume with the bulk of the $^3$H-labeled carbohydrate chains. The experiment also demonstrated that the smaller carbohydrate chains released after protease treatment do not owe their size to remnant proteins eluting in that size range, and that any crossover labeling of [$^3$H]-glucosamine into amino acids was insignificant, since no $^3$H-label elutes with degraded peptides. Both the carbohydrate chains in the void volume, as well as the smaller ones released after protease K digestion, failed to bind the nitrocellulose, when absorbed and washed by standard procedures for dot blot analysis. When similar amounts of the undegraded [$^3$H]-glycoprotein were absorbed, 20–25% bound irreversibly. Apparently the normal irreversible binding of these glycoproteins to nitrocellulose is dependent on the protein part of their structure. Thus, the failure of these glycoproteins to react with 43-9F antibody in immunoblot or dot blot analysis after protease K digestion does not necessarily indicate that amino acid sequences are involved in the epitope. This finding only shows that the epitope is associated with an amino acid sequence which is sensitive to protease K digestion.

The secreted glycoproteins were also incubated with endoglycosidase F (endo F), a glycosidase cleaving both complex and high mannose type glycans near their asparagine attachment sites in glycoproteins (Elder and Alexander, Proc. Natl. Acad. Sci. USA (1982) 79:4540–4544). Carbohydrate chains were produced having the same size as those after hydrolysis of the glycoproteins with protease K, but also large carbohydrates eluting with the void volume were maintained. (See the prior description relating to exclusion chromatography on Sephadex G25.) Control experiments showed that the conditions of hydrolysis were sufficient to cleave all carbohydrate from ribonuclease B, converting these molecules quantitatively to ribonuclease A. There was no apparent effect of the endo F on the antigenicity of 43-9F antigen as indicated in a dot blot assay. It follows that the large glycoconjugates eluting in the void volume, resistant to hydrolysis by endo F, contain most of the epitope recognized by 43-9F antibody.

To further define the sizes of the glycoproteins recognized by the 43-9F monoclonal antibody (Mab), proteins solubilized in the Triton X-100 extracts of RH-SLC-L11 cells and also the glycoproteins shed by these cells were analyzed by chromatography on Sephacryl S-400 (particle exclusion limit ~10×10$^6$d). Most of the [$^3$H]-glycosamine labeled glycoproteins from the cell extract eluted in a peak between the IgM and ovalbumin markers, 880,000 and 45,000d, respectively, and similarly the major antigenic components recognized in dot blot assay nearly overlapped this glycoprotein distribution. However, a minor part of the labeled macromolecules and the 43- 9F antigen eluted in the void volume indicating a very large size. This distribution was similar when the proteins were analyzed directly from the Triton X-100 extract, boiled in SDS containing solutions before analysis, or analyzed on a column equilibrated with 4.0M guanidine thiocyanate indicating that the large macromolecules are not aggregates. By contrast, the glycoproteins and the 43- 9F antigens shed into culture media were predominantly like the minor component of the extract, eluting at or near the void volume. It is likely that molecules in the trailing fractions having smaller sizes include degradation products. This has not been clearly defined, but it was noted that the amount of material in the trailing fractions increases after prolonged storage at 4° C.

43-9F Antibody Recognizes a Specific Carbohydrate

Radioimmune assays were established to examine the binding of $^{125}$I-labeled 43- 9F antibody to 43- 9F antigen in the presence of different competitors. Purified RH-SLC-L11 released glycoproteins were absorbed to the surface of plastic microtiter wells for radioimmune assay. After blocking non-specific absorbing sites each well was incubated for 4 hr with $^{125}$I-labeled 43- 9F antibody in 50μl PBS containing 1% FCS. Variable amounts of purified [$^3$H]-glucosamine labeled RH-SLC-L11 released glycoproteins or carbohydrates purified from the same labeled glycoproteins were added as competitors with the labeled antibody. After incubation and washing, the bound $^{125}$I-labeled antibody in each well was counted in a gamma counter. The 43- 9F antigen itself was used as a competitor, as were also the carbohydrate chains purified from the specific glycoproteins after proteolysis of the associated protein. All competitors were derived from the same preparation of [$^3$H]-glucosamine labeled glycoproteins so that the relative amounts of added competitors could be accurately compared from the $^3$H-label. [$^3$H]-Carbohydrates eluting in the void volume of an S200 column after exhaustive degradation with protease K compete even more strongly than the intact glycoproteins, suggesting that the epitope recognized by 43- 9F antibody is contained in these carbohydrate chains. The enhanced competition by the large chain carbohydrates has been repeatedly observed, which rules out the possibility that the 43- 9F antibody is recognizing an amino acid sequence sensitive to protease K. The smaller chain carbohydrates liberated after proteolysis of the glycoproteins also competed in binding the 43- 9F antibody but more weakly than the intact glycoproteins. Comparison of the competition data indicates that the concentration of the 43- 9F epitope is 2.5 to 6 fold lower per [$^3$H]-glucosamine residue in the smaller chain carbohydrates than in those eluting in the void volume. From these results it seems clear that the epitope recognized by the 43- 9F antibody is a carbohydrate sequence, specifically elaborated by the RH-SLC-L11 cells.

The 43- 9F epitope could not be found on a panel of human erythrocytes representing a variety of blood group antigens (A,B,O,M,N,S,s,P$_1$,C$^w$,E,c,e, Lu$^a$,-Lu$^b$,K,k,Kp$^a$,Kp$^b$,Le$^a$,Le$^b$,Fy$^a$,Jk$^a$,Jk$^a$,Vel, Wr$^a$,Co$^a$,-Co$^b$,Bu$^a$,Bg$^a$) as tested by direct and indirect agglutination and by dot-blot analysis on solubilized membrane preparations ("white ghosts").

Modulation of the 43- 9F Antigen

Exposure of the cultured RH-SLC-L11 cells to the 43- 9F antibody for >12 hr at room temperature or at 37° C. results in some, but variable reduction of the isotope from the cell surface as tested by FACS.

The antigenic modulation phenomenon which has also been seen with other cell surface antigens (see, for review, Chatenoud and Bach, *Immunology Today* (1984) 5:20–25) could be visualized ultrastructurally. RH-SLC-L11 cells were incubated with 43- 9F antibody for 30 min at 4° C., then incubated with biotinylated rabbit-anti-mouse Ig for another 30 min at 4° C., and finally with gold-conjugated avidin for another 30 min at 4° C. The culture was then divided into several subcultures that were incubated at 37° C. for various time periods prior to fixation in glutaraldehyde and processed for conventional electron microscopy. The surfaces of RH-SLC-L11 cells have multiple vesicles and an abundance of pseudopodias and microvilli. Gold particles were found on many of these structures, indicating 43- 9F epitopes were situated there. The gold particles could be detected inside the cells after 4 hr of incubation at 37° C., whereas incubation at 4° C. for 4 hr resulted in attachment of gold particles only to the cell surface membrane, but not within the cells. It therefore seems that at least a part of the modulation process as mediated by antibody can be due to internalization of the antibody-antigen complex.

In accordance with the subject invention, antibodies and their complementary antigens are provided which are specifically related to human squamous lung carcinoma. The antigens are glycoproteins, where the whole glycoprotein or fragments thereof, including the epitopic site of interest, may be employed by themselves or in conjunction with complementary antibodies as reagents in diagnostic assays. In addition, the antibodies may find use in in vivo imaging and therapy. The antibodies can also be used in cytology of biopsies for the detection of the presence of the antigen in the tissue. More importantly, the presence of the tumor marker may be found in the blood as indicative of the existence of a squamous lung carcinoma. Thus, it may be feasible to not only detect at an early stage the existence of squamous lung carcinoma cells in a human host, but to further detect their specific location in the human host. In addition, antibodies to the antigen may be detected as indicative of the existance of squamous lung carcinoma or its recurrence.

Although the foregoing invention has been described in some detail by way of illustration and example for purposes of clarity of understanding, it will be obvious that certain changes and modifications may be practiced within the scope of the appended claims.

I claim:

1. A monoclonal antibody specific for a glycoprotein which is a marker for human squamous lung carcinoma, where the marker is a carbohydrate sequence found on a plurality of glycoproteins in excess of about 50kDal and substantially absent in (1) carcinomas of organs other than lung, (2) leukemias and (3) sarcomas; and wherein said monoclonal antibody specific for a glycoprotein binds to the saccharide portion of said glycoprotein which is recognized specifically by IgM monoclonal antibody designated 43-9F secreted by hybridoma cell line having deposit no. ECACC 85013101.

2. A monoclonal antibody according to claim 1, wherein said monoclonal antibody is a human monoclonal antibody.

3. A monoclonal antibody according to claim 1 of the isotype IgM.

4. A monoclonal antibody according to claim 1, wherein said monoclonal antibody is a mouse monoclonal antibody.

5. A monoclonal antibody according to claim 4 of the isotype IgM.

6. A fragment of a monoclonal antibody according to claim 1, including at least the $F_v$ portion.

7. A monoclonal antibody specific for the idiotype of a glycoprotein binding monoclonal antibody according to claim 1.

8. A monoclonal antibody according to claim 7, wherein said glycoprotein binding monoclonal antibody is a human monoclonal antibody.

9. An IgM monoclonal antibody designated 43-9F secreted by a hybridoma cell line having deposit no. ECACC 85013101.

10. An isolated, purified polysaccharide characterized as being present in glycoproteins released by human squamous lung cancer cells, said glycoproteins being of less than about 250kDal, and binding specifically to a monoclonal antibody according to claim 9.

11. An isolated, purified polysaccharide according to claim 10, of less than about 45kDal.

12. An isolated, purified glycoprotein composition comprising glycoproteins of from about 50kDal to about 1mDal capable of binding to a monoclonal antibody according to claim 9, derived from human squamous lung cancer cells and substantially free of other human squamous lung cancer cell glycoproteins and proteins.

13. A glycoprotein composition according to claim 12, purified by chromatography on a gel permeation column and eluting with phosphate buffered saline containing a small amount of a non-ionic detergent.

14. A monoclonal antibody prepared in immunogenic response to a glycoprotein composition according to claim 12.

15. An immortalized B-lymphocytic cell line secreting a monoclonal antibody according to claim 1.

16. An immortalized B-lymphocytic cell line according to claim 15, wherein said cell line is a human cell line.

17. An immortalized B-lymphocytic cell line according to claim 15, wherein said cell line is a mouse cell line.

18. An immortalized B-lymphocytic cell line according to claim 17, wherein said cell line is hybridoma cell line designated 43- 9F having deposit no. ECACC 85013101.

19. An immortalized B-lymphocytic cell line secreting a monoclonal antibody according to claim 7.

20. A method for detecting the presence of squamous lung cancer in a human host, which comprises:
   combining a sample from said human host suspected of having a polysaccharide according to claim 10 or endogenous antibodies to said polysaccharide with monoclonal antibodies specific for said polysaccharide or the idiotype of said endogenous antibodies; and
   detecting the formation of immune complexes as indicative of the presence or prior presence of squamous lung cancer cells.

21. A method according to claim 20, wherein said sample is blood or serum.

22. A method according to claim 20, wherein said method is the dot-blot method.

23. A method according to claim 20, wherein said monoclonal antibody or a second antibody to said monoclonal antibody is conjugated to a label capable of providing a detectable signal.

24. A method according to claim 23, wherein said label is a radionuclide, fluorescer or enzyme.

25. A kit for use in a method for detecting the presence of squamous lung cancer in a human host comprising a monoclonal antibody according to claim 1 or 7, wherein said monoclonal antibody is conjugated to a label capable of providing a detectable signal or a second antibody to one of said monoclonal antibodies is includes, wherein said second antibody is conjugated to a label capable of providing a detectable signal, and a composition including a polysaccharide specifically binding to IgM monoclonal antibody designated 43-9F secreted by hybridoma cell line having deposit no. ECACC 85013101.

26. A monoclonal antibody according to claim 1 conjugated directly or indirectly to a label capable of providing a detectable signal.

27. A monoclonal antibody according to claim 26, wherein said label is a radionuclide, fluorescer or enzyme.

* * * * *